US006415171B1

United States Patent
Gueziec et al.

(10) Patent No.: US 6,415,171 B1
(45) Date of Patent: Jul. 2, 2002

(54) SYSTEM AND METHOD FOR FUSING THREE-DIMENSIONAL SHAPE DATA ON DISTORTED IMAGES WITHOUT CORRECTING FOR DISTORTION

(75) Inventors: Andre Gueziec, Mamaroneck; Alan David Kalvin, Irvington, both of NY (US); Willie Williamson, Jr., Roseville, CA (US)

(73) Assignee: International Business Machines Corporation, Armonk, NY (US); .

( * ) Notice: Subject to any disclaimer, the term of this patent is extended or adjusted under 35 U.S.C. 154(b) by 0 days.

(21) Appl. No.: 09/354,800

(22) Filed: Jul. 16, 1999

(51) Int. Cl.[7] .................................................. A61B 5/05
(52) U.S. Cl. ...................................... 600/407; 600/425
(58) Field of Search ................................ 600/407, 424, 600/416, 417, 426, 427, 429, 439, 437; 606/130; 378/205–207; 382/128, 131; 345/427; 128/916, 920, 922, 923

(56) References Cited

U.S. PATENT DOCUMENTS

| | | | | |
|---|---|---|---|---|
| 5,299,288 A | * | 3/1994 | Glassman et al. | 606/130 |
| 5,445,166 A | * | 8/1995 | Taylor | 128/897 |
| 5,495,576 A | * | 2/1996 | Ritchey | 395/125 |
| 5,531,227 A | * | 7/1996 | Schneider | 600/407 |
| 5,638,819 A | * | 6/1997 | Manwaring et al. | 600/407 |
| 5,711,299 A | * | 1/1998 | Manwaring et al. | 600/407 |
| 5,951,475 A | * | 9/1999 | Gueziec et al. | 600/425 |
| 6,019,724 A | * | 2/2000 | Gronningsaeter et al. | 600/439 |
| 6,167,292 A | * | 12/2000 | Badano et al. | 600/407 |
| 6,201,984 B1 | * | 3/2001 | Funda et al. | 600/407 |

* cited by examiner

Primary Examiner—Brian L. Casler
(74) Attorney, Agent, or Firm—Louis J. Percello, Esq.; McGinn & Gibb, PLLC

(57) ABSTRACT

A system and method for intra-operatively providing a surgeon with visual evaluations of possible surgical outcomes ahead of time, and generating simulated data, includes a medical imaging camera, a registration device for registering data to a physical space, and to the medical imaging camera, and a fusion mechanism for fusing the data and the images to generate simulated data, without correcting for distortion. The simulated data (e.g., such as augmented X-ray images) is natural and easy for a surgeon to interpret. In an exemplary implementation, the system preferably includes a data processor which receives a three-dimensional surgical plan or three-dimensional plan of therapy delivery, one or a plurality of two-dimensional intra-operative images, a three-dimensional model of pre-operative data, registration data, and image calibration data. The data processor produces one or a plurality of simulated post-operative images, without correcting for distortion, by integrating a projection of a three-dimensional model of pre-operative data onto one or a plurality of two-dimensional intra-operative images.

17 Claims, 4 Drawing Sheets

SYSTEM AND METHOD FOR FUSING THREE-DIMENSIONAL SHAPE DATA ON DISTORTED IMAGES WITHOUT CORRECTING FOR DISTORTION

CROSS-REFERENCE TO RELATED APPLICATION

The present application is related to U.S. patent application Ser. No. 09/299,643, filed on Apr. 27, 1999, to Gueziec et al., entitled "SYSTEM AND METHOD FOR INTRA-OPERATIVE, IMAGE-BASED, INTERACTIVE VERIFICATION OF A PRE-OPERATIVE SURGICAL PLAN" having IBM assigned to the present assignee, and incorporated herein by reference.

This invention was made with Government support under control number 70NANB5H1088 awarded by the NIST Advanced Technology Program (ATP). The Government has certain rights in the invention.

BACKGROUND OF THE INVENTION

1. Field of the Invention

The present invention generally relates to robotics and medical imaging techniques and, more particularly to robotically-assisted surgical systems and other devices incorporating methods for registering image data (both pre-operative and intra-operative) to physical space and for providing feedback, and in particular visual feedback, to the clinician.

2. Description of the Related Art

Computers are increasingly used to plan complex surgeries by analyzing pre-operative Computed Tomography (CT) or Magnetic Resonance Imaging (MRI) scans of a patient.

To execute the surgical plan, it is important to accurately align or register the three-dimensional pre-operative and intra-operative data to an actual location of the patient's anatomical features of interest during surgery.

One conventional technique for performing this type of registration is to attach a stereo-tactic frame or fiducial markers to the patient, and to precisely locate the frame or markers prior to and during surgery.

For example, in the case of a surgery involving a patient's femur, a conventional registration protocol includes implanting three metallic markers or pins in the patient's femur (e.g., one proximally in the trochanter and two distally in the condyles, near the knee). However, the insertion of the pins requires minor surgery. A CT-scan image of the patient is subsequently acquired. By analyzing the CT data, the surgeon decides upon the size and location of the implant that best fits the patient's anatomy. During surgery, the metallic pins are exposed at the hip and knee. The patient's leg is attached to a surgical robot device that then must locate the exposed pins. A registration, or coordinate transformation from CT space to robot space, is computed using the locations of the three pins as a Cartesian frame. The accuracy of this registration has been measured to be better than one millimeter. This conventional registration protocol is described in U.S. Pat. No. 5,299,288 entitled "IMAGE-DIRECTED ROBOTIC SYSTEM FOR PRECISE ROBOTIC SURGERY INCLUDING REDUNDANT CONSISTENCY CHECKING" by Glassman et al., and incorporated herein by reference.

However, using such pins as markers is not always desirable, as they may cause significant patient discomfort, and the required surgical procedure to insert and subsequently remove the pins is inconvenient and costly to the patient.

An alternative registration technique is to perform anatomy-based registration that uses anatomical features of the patient (e.g., generally bone features), as markers for registration. Conventional methods for performing anatomy-based registration are described in "Registration of Head CT Images to Physical Space Using a Weighted Combination of Points and Surfaces" by Herring et al., in *IEEE Transactions on Medical Imaging*, Vol. 17, No. 5, pages 753–761, 1998 and in U.S. patent application Ser. No. 08/936,935 entitled "METHODS AND APPARATUS FOR REGISTERING CT-SCAN DATA TO MULTIPLE FLUOROSCOPIC IMAGES", filed on Sep. 27, 1997 by A Gueziec et al., each of which is herein incorporated by reference in its entirety.

Once the registration has been performed, it is important to provide the clinician with means to assess the registration, allowing him or her to validate, reject or improve the registration (and the surgical plan). A system and method for advising a surgeon is described in U.S. Pat. No. 5,445,166, entitled "SYSTEM FOR ADVISING A SURGEON", by Taylor, which is herein incorporated by reference in its entirety. Taylor describes a system for guiding the motions of a robot, or of a positioning device controlled by motors, and teaches how audio feedback and force feedback can be provided to a surgeon. Taylor also describes a visual adviser allowing comparison of the surgical plan with its execution. The system taught by Taylor optionally uses a camera at the end of a surgical instrument that sends an image to the graphics adapter, optionally mixed with graphics output of the computer.

A conventional technique for simulating a post-operative X-ray image is described in "An Overview of Computer-Integrated Surgery at the IBM T. J. Watson Research Center" by Taylor et al., in *IBM Journal of Research*, 1996, which is herein incorporated by reference in its entirety.

Thus, conventional techniques are useful for registering three-dimensional pre-operative and intra-operative data to an actual location of anatomical features of interest during surgery, and to provide advice to the surgeon. However, none of the conventional techniques teaches how to simulate a post-operative condition depending upon the registration of image data to physical space, by fusing intra-operative images with registered pre-operative data, and generating new images.

In Taylor et al., the simulated post-operative X-ray image is generated using only pre-operative CT (Computed Tomography) data. Herring et al. do not teach how to evaluate the registration accuracy intra-operatively.

Although Glassman et al.'s and Taylor's systems compare a surgical plan and its execution, neither Glassman et al. nor Taylor teaches how to simulate the outcome of a surgical plan prior to the actual execution of the plan. With Taylor's system, a surgeon can take corrective measures to minimize the effects of a wrongful execution of the plan, but cannot make a decision before any execution of the plan and therefore cannot prevent all errors before they occur.

Further, the information produced by Taylor's system for advising a surgeon is not represented in the form of conventional medical media (e.g., such as X-ray images) and requires an extra burden on the surgeon in order to interpret and evaluate this information.

Thus, it is believed that conventional techniques do not exist (or at the very least are inadequate) for (a) providing the surgeon with post-operative evaluations prior to surgery, that are obtained by merging intra-operative image data and pre-operative data, and (b) presenting such evaluations in a standard clinical fashion (e.g., such as augmented X-ray images) that is natural for a surgeon to interpret.

Other problems of the conventional systems and methods include the limited availability of 2-D/3-D registration methods in conventional art systems for advising a surgeon.

In another conventional system, as described in the above-mentioned U.S. patent application Ser. No. 09/299,643, the geometric distortion of an X-ray image is always corrected. This is problematic because a clinician or surgeon is used to seeing the unmodified image (e.g., an image with distortion). That is, as a practical matter, surgeons generally are not familiar with seeing the modified image. Surgeons are used to interpreting the unmodified images. Further, such a correction may cause image degradation or blurring due to the reformatting of the image. Additionally, slower and more complex processing results from the image correction process.

SUMMARY OF THE INVENTION

In view of the foregoing and other problems of the conventional methods and structures, an object of the present invention is to provide a method and structure for intra-operatively providing the surgeon with visual evaluations of possible surgical outcomes ahead of time, the evaluations being obtained by merging intra-operative image data and pre-operative data, and presented in a standard clinical fashion (e.g., such as augmented X-ray images) that is natural and easy for a surgeon to interpret.

Another object of the present invention is to provide a system and method for fusing three-dimensional shape data on distorted images without correcting for distortion.

Yet another object of the present invention is to provide a system and method for assisting the surgeon in improving an inaccurate registration of a pre-operative surgical plan to a physical space of an operating room.

Still another object of the present invention is to provide an improved robotically assisted surgical system that also provides visual post-operative evaluations.

A further object of the present invention is to provide an improved robotically-assisted surgical system that includes a system for assisting the surgeon in improving a registration.

Another object of this invention is to provide an improved robotically assisted surgical system that includes a system for preventing surgical errors caused by internal failure of the robot's calibration system.

In a first aspect of the present invention, a system is provided for fusing three-dimensional shape data on distorted images without correcting for distortion.

The inventive system preferably includes a data processor. The data processor takes as inputs a three-dimensional surgical plan or three-dimensional plan of therapy delivery, one or a plurality of two-dimensional intra-operative images, a three-dimensional model of pre-operative data, registration data, and image calibration data.

The data processor produces one or a plurality of simulated post-operative images, by integrating a projection of a three-dimensional model of pre-operative data onto one or a plurality of two-dimensional intra-operative images, without correcting for any distortion in the images.

The data processor optionally receives an input from a surgeon or a clinician. The input preferably includes a set of constraints on the surgical plan or plan of therapy delivery. The data processor preferably optimizes the surgical plan or plan of therapy delivery using the constraints.

In another aspect of the present invention, a system (and method) for generating simulated data, includes a medical imaging camera for generating images, a registration device for registering data to a physical space, and to the medical imaging camera, and a fusion (integration) mechanism for fusing (integrating) the data and the images, without correcting for distortion to generate simulated data.

In yet another aspect of the invention, a method of fusing three-dimensional image data on distorted images, includes receiving a potentially distorted image, calibrating the potentially distorted image, based on the calibration, computing an apparent contour of the three-dimensional shape of the potentially distorted image, for each pixel of the image, determining a ray in 3-dimensional space and computing a distance from the ray to the apparent contour, and selectively adjusting a pixel value of the potentially distorted image based on the distance.

In yet another aspect of the invention, a signal-bearing medium is provided for storing a program for performing the method of the invention. Other aspects of the invention are also set forth below.

With the invention, the surgeon is provided with intra-operative visual evaluations of possible surgical outcomes in advance, with the evaluations being obtained by merging intra-operative image data and pre-operative data. Such evaluations are presented in a standard clinical fashion that is natural and easy for a surgeon to interpret. Further, the inventive system compares several registration methods of pre-operative data to the physical space of the operating room.

Moreover, the invention assists the surgeon in improving an inaccurate registration of a pre-operative surgical plan to the physical space. Additionally, the system can be robotically-assisted and can provide visual post-operative evaluations.

Additionally, in the robotically-assisted implementation of the inventive system, surgical errors, caused by internal failure of the robot's calibration system, can be prevented.

Further, with the invention, a clinician or surgeon can view images in the manner that they are accustomed. That is, the clinician or surgeon can view the unmodified image (e.g., an image with distortion), in the manner with which they are familiar. Thus, the surgeons can continue to interpret the unmodified images, as is customary. Further, since no correction is performed as in the conventional system and methods, no image degradation or blurring results from such image correction and reformatting of the image. Additionally, processing speed is not decreased, and similarly processing resources are not increased since the processing of the method of the present invention is less complex than that of the conventional systems and methods.

BRIEF DESCRIPTION OF THE DRAWINGS

The foregoing and other purposes, aspects and advantages will be better understood from the following detailed description of preferred embodiments of the invention with reference to the drawings, in which.

DETAILED DESCRIPTION OF PREFERRED EMBODIMENTS OF THE INVENTION

Figure 1:
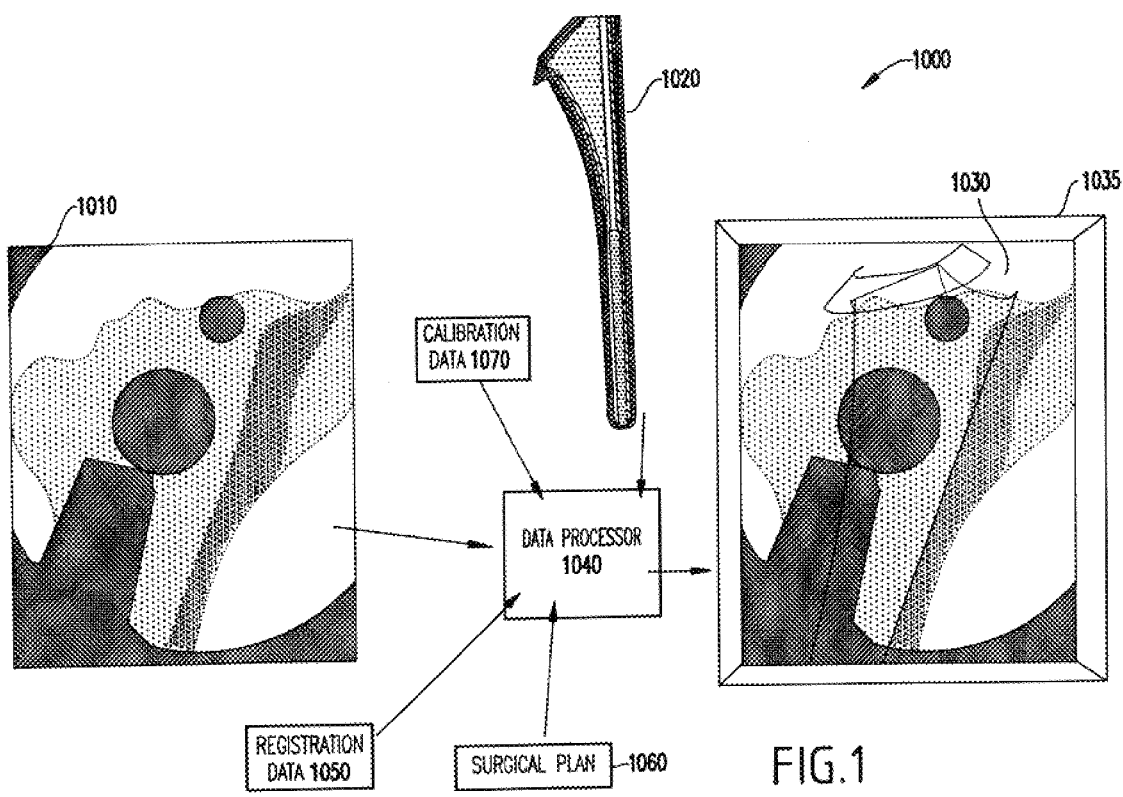
FIG. 1 is a block diagram of a preferred embodiment of a system according to the present invention.

Referring now to the drawings, and more particularly to FIGS. 1–8, there is shown a preferred embodiment of the method and structure according to the present invention.

Generally, the present invention resides in a system and method to intra-operatively provide the surgeon with visual evaluations of possible surgical outcomes ahead of time, the evaluations being obtained by merging intra-operative image data and pre-operative data, and being presented in a standard clinical fashion (such as augmented X-ray images) that is natural and easy for a surgeon to interpret.

The present invention differs from the invention in U.S. patent application Ser. No. 09/299,643 by omitting the step of correcting the geometric distortion of the X-ray image in the method of U.S. patent application Ser. No. 09/299,643 (e.g., step 2040 in FIG. 2 thereof) and other processing as described below.

That is, the step of correcting the geometric distortion of the X-ray image is omitted between the step of obtaining registration information from the X-ray image to the pre-operative CT image and the step of using the registration and calibration information to project pre-operative data on the X-ray image.

A novel aspect of the present invention is to allow intra-operative manipulation of a model (e.g., such as a CAD model of an implant) as opposed to a real object (e.g., such as a cutter of a surgical robot as in Taylor's system).

Referring to FIG. 1, a system 1000 according to the present invention uses a two-dimensional intra-operative image 1010 (e.g., a two-dimensional X-ray or other type of image) and a three-dimensional shape of a prosthetic implant 1020, and comprises a data processor 1040. The pre-operative image (e.g., of the shape of the implant with respect to anatomical features) may be obtained by an X-ray, computed tomography (CT) scanner, whereas the intra-operative image(s) may be obtained by a two-dimensional (2D) X-ray camera.

The data processor 1040 receives the image 1010 and the shape 1020, as well as registration data 1050 and a surgical plan 1060. The registration data registers the shape 1020 with the camera used for acquiring the image 1010. An example of registration process producing registration data 1050 is provided in the above-mentioned U.S. patent application Ser. No. 08/936,935, previously incorporated by reference.

A typical example of the surgical plan 1060 is a planned type, orientation and position of an implant relative to anatomical structures in a pre-operative CT scan. Another example of the surgical plan 1060 is the planned type, orientation and position of an implant relative to co-registered intra-operative X-ray images of anatomical structures.

Image calibration data 1070 is also input to the data processor. The data processor 1040 produces a simulated post-operative image 1030. Image 1030 may be presented visually to the surgeon on a display 1035. That is, the post-operative simulation (e.g., data which preferably includes an image such as a 2-dimensional image) may be displayed on any of a cathode ray tube (CRT), liquid crystal display (LCD), or the like.

Referring now to FIGS. 2–6, the operation of the present invention will be described hereinbelow.

Figure 2:
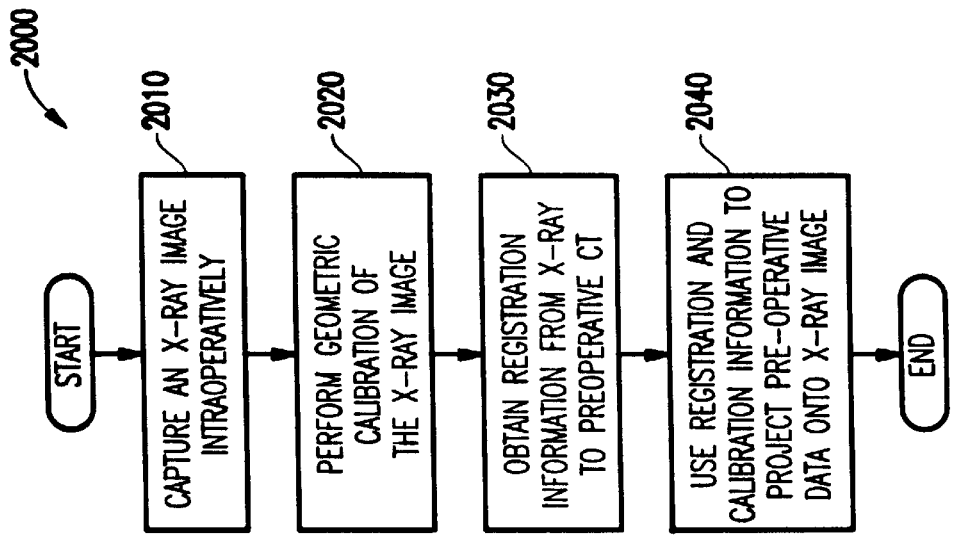
FIG. 2 is a flow chart showing an overview of a process to generate a post-operative simulation.

FIG. 2 is a flow chart illustrating how a post-operative simulation can be generated using a method 2000 according to the present invention.

In Step 2010, an image (e.g., an X-ray image or other intra-operative image 1010 as shown in FIG. 1) is captured intra-operatively. Conventional methods for capturing an X-ray image include using a frame grabber connected to the video output of a conventional fluoroscope. Fluoroscopes are manufactured by many medical imaging equipment manufacturers. An example of a fluoroscope is the Ziehm Exposcop Plus® System (Exposcop Plus is a trademark of the Ziehm Corporation). Another method for capturing an X-ray image intra-operatively is to use an X-ray flat panel detector. An example of an X-ray flat panel detector is the FlashScan 30®. FlashScan 30 is a trademark of the DPIX Corporation.

Then, in Step 2020, a geometric calibration of the X-ray image is performed. Geometric calibration is preferably performed using the teachings of the above-mentioned U.S. patent application Ser. No. 08/936,935.

In Step 2030, X-ray and pre-operative CT data are registered (e.g., this data represents the registration data 1050 of FIG. 1). A preferred method for registering X-ray and pre-operative CT data is described in the above-mentioned U.S. patent application Ser. No. 08/936,935.

Then, in Step 2040, without correcting for the geometric distortion of the X-ray image as in the above mentioned method in U.S. patent application No. 09/299,643, the registration and calibration are used to project pre-operative data such as a three-dimensional shape of an implant (e.g., shape 1020 in FIG. 1) onto the X-ray image. The result is the simulated post-operative image 1030 in FIG. 1.

Figure 3:
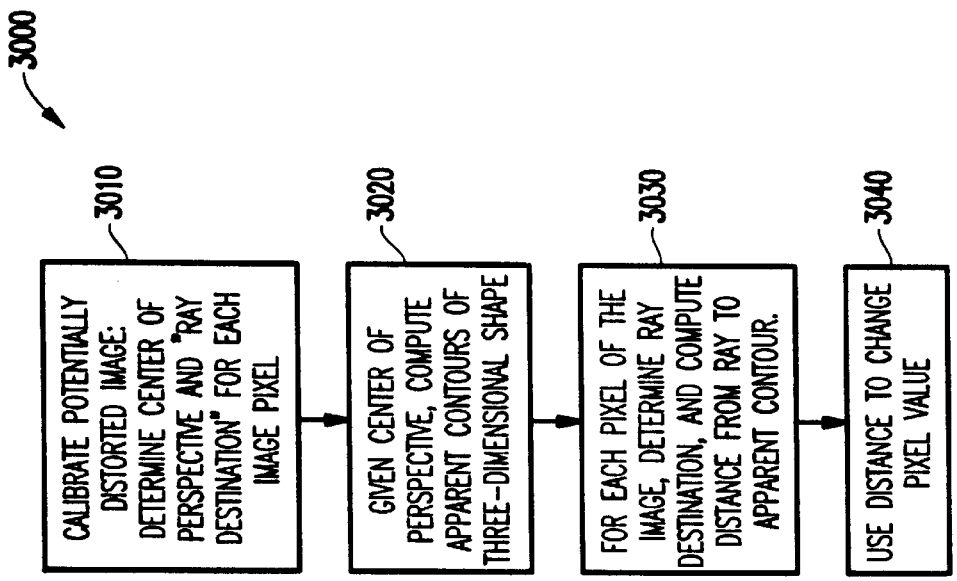
FIG. 3 is a flow chart showing an overview of a process for fusing three-dimensional shape data on distorted image without correcting for distortion.

Essentially, when bypassing the step of reformatting the image (e.g., correcting the image for distortion), the shape may be superimposed on the image that is still distorted. The following steps, as shown in FIG. 3, are equivalent to applying the same distortion present in the image when projecting the three-dimensional shape onto it. The shape is projected onto the image and the projection process incorporates a distortion process, which becomes complex.

Figure 4:
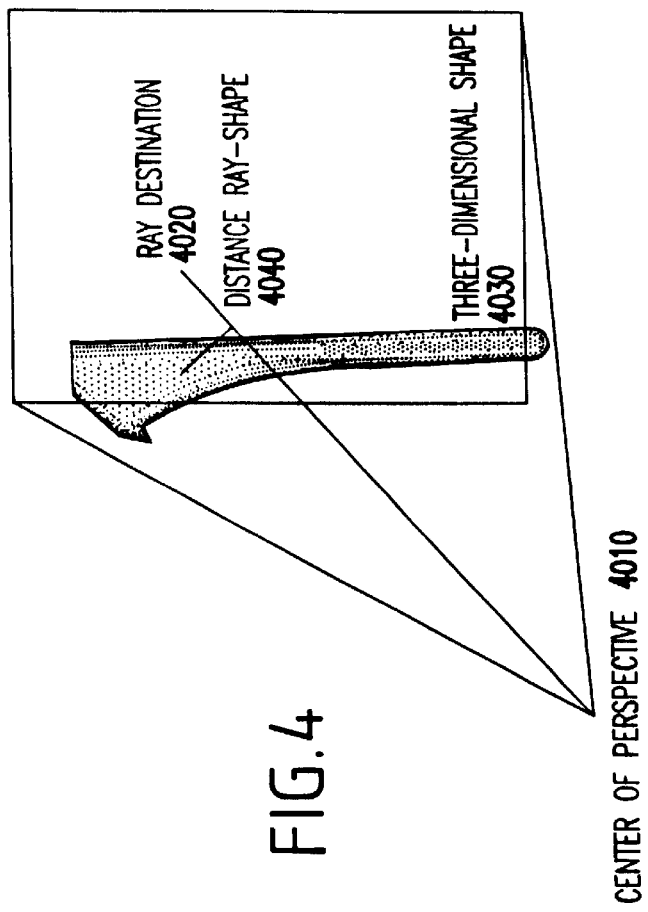
FIG. 4 illustrates a technique of finding a center of perspective of a three-dimensional shape (e.g., implant) to the image and a ray destination for each pixel of the image.

In Step 3010, an image (e.g., X-ray image) that is potentially distorted, is calibrated. To perform calibration, a system is used for associating a center of perspective 4010 (e.g., as shown in FIG. 4) to the image and for determining a "ray destination" 4020 for each pixel of the image. For example, the system described in the above-mentioned U.S. patent application Ser. No. 08/936,935 could be used for this purpose.

In Step 3020, a set of three-dimensional apparent contours is computed knowing the center of perspective 4010 (e.g., FIG. 4) and the three-dimensional shape 4030 is decomposed into sub-shapes (e.g., triangles as shown in greater detail in FIGS. 5 and 6 discussed further below).

The processing for decomposing the apparent contour into triangles is further described in U.S. patent application Ser.

No. 09/236,688, entitled "SYSTEM AND METHOD FOR FINDING THE DISTANCE FROM A MOVING QUERY POINT TO THE CLOSEST POINT ON ONE OR MORE CONVEX OR NON-CONVEX SHAPES", by A. Gueziec, filed on Jan. 25, 1999 as IBM incorporated herein by reference in its entirety. Other shapes be used instead of or in addition to triangles. For example, polygonal shapes could be used instead of or in addition to triangles, as would be known by one of ordinary skill in the art taking the present application as a whole.

Given the center of perspective (possibly very far such as, for example, 1 meter for X-rays; of course, such a distance depends on the focal length of the imaging camera and could be more for another imaging camera source) from the surface, three-dimensional apparent contours are defined and extracted as follows. It is noted that it is possible to have only one apparent contour depending upon the shape involved in the viewing direction. Generally, a complex curve has visible and invisible edges as shown in FIGS. 5 and 6.

Figure 5:
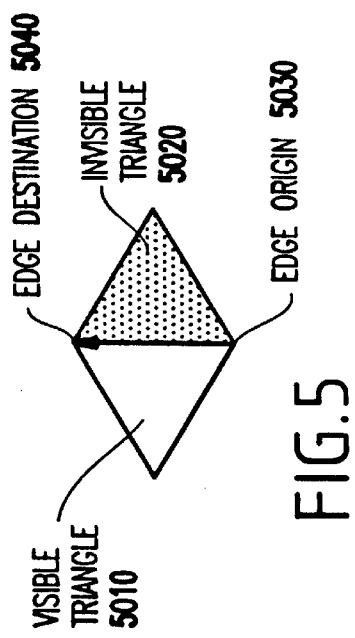
FIG. 5 is a schematic diagram for explaining the decomposition of a shape into visible and invisible sub-shapes (e.g., triangles) which are separated by apparent contours.
Figure 6:
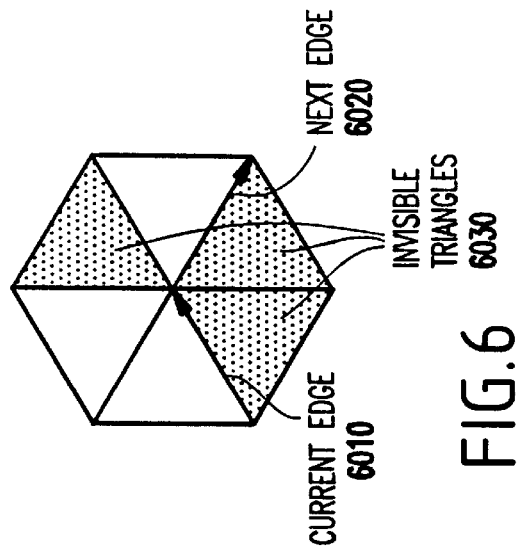
FIG. 6 is a schematic diagram for explaining a "current edge" and a "next edge" in the process of obtaining the apparent contours.

That is, as shown in FIGS. 4–6, for each surface triangle, the "viewing direction" is defined as the vector originating from the center of perspective to the triangle centroid.

If the triangle normal (e.g., defined by the cross product of ordered oriented triangle edges, as generally known by one of ordinary skill in the art of computer graphics) makes an obtuse angle with the viewing direction, the triangle is considered "visible". Otherwise, it is considered "invisible".

Surface apparent contours are a subset of surface edges, such that the triangle on one side of the edge is visible and the triangle on the other side of the edge is invisible.

Referring to FIG. 5, an example of a visible triangle and invisible triangle are shown. That is, a visible triangle 5010 and an invisible triangle 5020 are illustrated in FIG. 5. The apparent contours are such that the edges are linked to form (non-planar) closed polygonal curves in three dimensions.

To build the apparent contours, all edges, belonging to any apparent contour using the criterion defined above, are identified, and such edges are added to a list (e.g., a table or register with various edges input thereto). The edges are oriented such that the visible triangle is on the left side of the edge, thus defining an edge origin 5030 and an edge destination 5040.

Then, the following process is iterated. For clarity, the reader is referred to FIG. 6.

That is, first, the first edge in the list is taken, and a new apparent contour is created starting with that edge (e.g., step 1).

Then, the apparent contour, containing that edge, is completed as follows (e.g., step 2). Starting from the destination of a current edge 6010, a next edge 6020 is determined. The triangles, incident to the destination vertex in a counter-clockwise fashion (e.g., just a convention; a clockwise direction could alternatively be employed), are visited, and the first edge is determined that belongs to the list of apparent contour edges. This is necessary because there may be several such edges. Step 2 above is re-applied (e.g., reiterated) until the next edge is the same as the first edge that was processed in step 1.

In a third step, all the edges forming that contour from the list of apparent contour edges, are removed. Then, steps (1) to (3) are re-applied until the list of apparent contour edges is empty.

Then, in Step 3030 of Step 3 for each pixel of the potentially distorted image, the corresponding ray (e.g., line) from the center of perspective is determined, and the distance to the apparent contours is computed. The distance from a given line in three-dimensions to an apparent contour, which is a particular type of curve in three-dimensions may be preferably computed as follows.

First, the teachings of the above-mentioned U.S. patent application Ser. No. 09/236,688, incorporated herein by reference, may be applied.

In the above-mentioned patent application, one of the steps uses a method for computing the distance from a point to a line segment in three-dimensional space. This method should be replaced with a method for computing the distance from a line in three-dimensions to a line segment in three-dimensions. Various conventional methods may be used for this purpose, that are known to those skilled in the art. Such a method is described on p.10 of "Locally Toleranced Surface Simplification", A. Gueziec, *IEEE Transactions on Visualization and Computer Graphics*, Vol 5, No. 2, 1999.

Finally, in Step 3040, the distance ray-shape 4040 that was determined in the previous step, is used to update the pixel value. Various correspondences between distance values and pixel values may be used for this purpose. The correspondence used in the above-mentioned U.S. patent application Ser. No. 09/299,643, incorporated herein by reference, may be used for this purpose.

Thereafter, a process for validating, rejecting or improving a surgical plan using post-operative simulations, as described in the above-mentioned U.S. patent application Ser. No. 09/299,643, incorporated herein by reference.

Figure 7A:
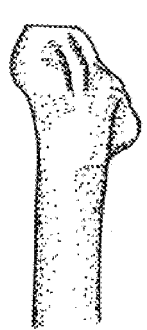
FIGS. 7A–7E illustrate a pre-operative model and FIGS. 7F–7H illustrate distorted images.
Figure 7B:
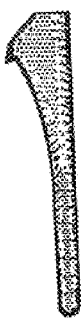
Figure 7C:
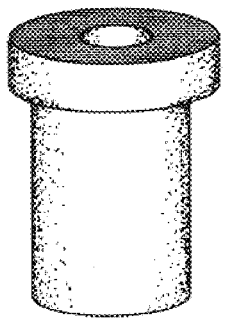
Figure 7D:
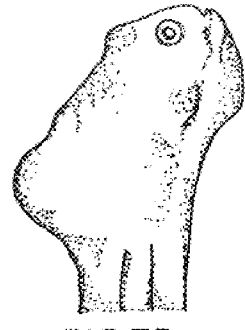
Figure 7E:
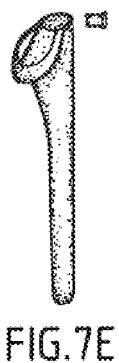
Figure 7F:
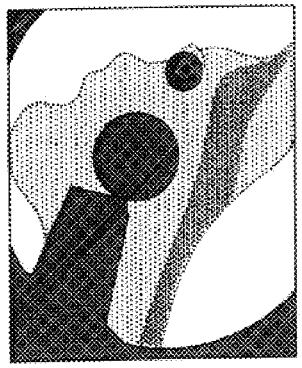
Figure 7G:
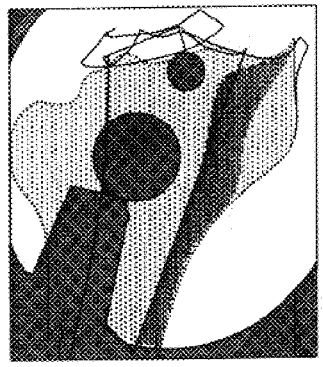
Figure 7H:
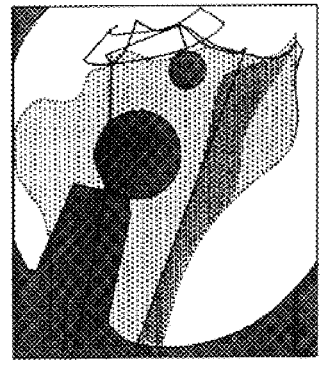

In an implementation of the above process, FIGS. 7A–7E illustrate a pre-operative model, in which FIG. 7A illustrates a CT-based proximal femur model, FIG. 7B illustrates an implant CAD model, FIG. 7C illustrates a simplified CAD Model of a fiducial pin (e.g., exemplary dimensions of 8 mm diameter by 10 mm), FIG. 7D illustrates a femur and pin model registered in CT space, and FIG. 7E illustrates an implant and pin model registered in CT space. FIGS. 7F–7H illustrates distorted images. That is, the projection of the shapes is distorted according to the image distortion model. FIG. 7F shows superimposing the proximal pin (e.g., anatomy-based registration) and that the pin model is longer than the physical pin. FIG. 7G show superimposing femur and implant models, wherein FIG. 7G is a marker based registration, whereas FIG. 7H shows an anatomy.

Thus, in the invention, for a given X-ray image, using calibration information, first a center of perspective is determined which is used to compute silhouette curves of the implant model (as explained in U.S. patent application Ser. No. 09/299,643). Then, the method works independently of whether distortion-corrected images or distorted images are produced.

That is, for each pixel of the X-ray image (original image pixels, or rectified image pixels), an X-ray path from the (u, v) (grid) coordinates corresponding to the pixel and the center of perspective are determined. Then, the distance is computed from each X-ray path to the implant or other shape as discussed in U.S. patent application Ser. No. 09/299,643.

Finally, the computed distances are converted to gray-scale values. Various methods can be used to do this. To produce the images, the following mapping was used: if the distance was less than 0.05 mm, a gray-scale value of 0 was used, otherwise, if the distance was less than 0.1 mm, a gray-scale value of 30 was used, otherwise, if the distance was less than 0.2 mm, a gray-scale value of 60 was used, and otherwise, no change to the existing gray-scale value was done. This method avoids "aliasing" in the implant outline (i.e., "staircase" effects in the resulting line drawings). One advantage of using distances to silhouette curves is that the resulting projection of the implant shows only the projected silhouette, which is sufficient to precisely indicate the position of the implant, but does not obscure any of the anatomy.

Figure 8:
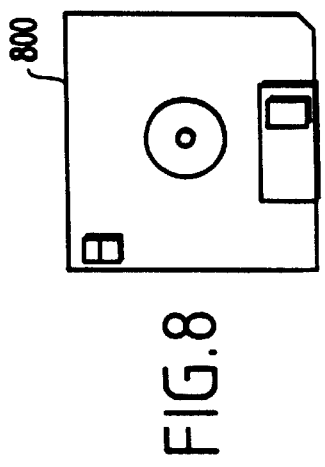
FIG. 8 illustrates a storage medium 800 for storing steps of the program for fusing three-dimensional shape data on a distorted image without correcting for distortion.

As shown in FIG. 8, in addition to the hardware and process environment described above, a different aspect of the invention includes a computer-implemented method for fusing three-dimensional shape data on distorted images without correcting for distortion, as described above. As an example, this method may be implemented in the particular hardware environment discussed above.

Such a method may be implemented, for example, by operating a CPU, to execute a sequence of machine-readable instructions. These instructions may reside in various types of signal-bearing media.

Thus, this aspect of the present invention is directed to a programmed product, comprising signal-bearing media tangibly embodying a program of machine-readable instructions executable by a digital data processor incorporating the CPU and hardware above, to perform a method of fusing three-dimensional shape data on distorted images without correcting for distortion.

This signal-bearing media may include, for example, a random access memory (RAM) contained within the CPU, as represented by a fast-access storage, for example. Alternatively, the instructions may be contained in another signal-bearing media, such as a magnetic data storage diskette 800 (FIG. 8), directly or indirectly accessible by the CPU.

Whether contained in the diskette 800, the computer/CPU, or elsewhere, the instructions may be stored on a variety of machine-readable data storage media, such as DASD storage (e.g., a conventional "hard drive" or a RAID array), magnetic tape, electronic read-only memory (e.g., ROM, EPROM, or EEPROM), an optical storage device (e.g. CD-ROM, WORM, DVD, digital optical tape, etc.), paper "punch" cards, or other suitable signal-bearing media including transmission media such as digital and analog communication links and wireless. In an illustrative embodiment of the invention, the machine-readable instructions may comprise software object code, compiled from a language such as "C", etc.

While the invention has been described in terms of several preferred embodiments, those skilled in the art will recognize that the invention can be practiced with modification within the spirit and scope of the appended claims.

It is noted that the present invention can be implemented in many applications.

For example, the invention can be used in orthopedic surgery (e.g., such as total hip replacement surgery, revision total hip replacement surgery, spine surgery, etc.). In one implementation, the pre-operative images typically are three-dimensional CT images or MRI (Magnetic Resonance Imaging) images, and the intra-operative images typically are X-ray fluoroscopy images. A three-dimensional pre-operative plan (e.g., such as planning position of a prosthetic implant with respect to the surrounding bony anatomy) may be integrated onto one or several two-dimensional X-ray images to provide the surgeon with images to evaluate a potential surgical outcome.

The present invention also can be used in treating cancer by radio-therapy. Conventional radio-therapy delivery devices include an imaging device (e.g., producing "portal" images), whereas the present invention can be used to project a three-dimensional radio-therapy plan onto two-dimensional images produced by the imaging device, thereby providing the clinician with a mechanism and technique to evaluate the accuracy with which the therapy will be delivered.

The present invention also can be used in brain surgery, in which case the pre-operative images typically may be three-dimensional CT or MRI images, and the intra-operative images typically may be X-ray images. A three-dimensional surgical plan (e.g., such as planning the removal of a tumor of a specified shape and location relatively to the surrounding imaged anatomy) may be integrated onto one or several two-dimensional X-ray images to provide the surgeon with images to evaluate a potential surgical outcome.

The present invention also can be used in craniofacial surgery. In such a case, the pre-operative images typically would be three-dimensional CT or MRI images, and the intra-operative images typically would be X-ray images. A three-dimensional surgical plan typically would involve osteotomies and the relocation of bone fragments to correct some physical deformities. A robotic device would be used to manipulate bone fragments. The three-dimensional plan would be integrated onto one or several two-dimensional X-ray images to provide the surgeon with images to evaluate a potential surgical outcome, and in particular to compare the resulting images with X-ray images of normal individuals, or to evaluate that the execution of the plan will be correct.

What is claimed is:

1. A radiographic imaging system for generating two-dimensional simulated radiographic images, comprising:
   a medical imaging device for generating two-dimensional radiographic images that are subject to distortion and comprise distorted two-dimensional radiographic images;
   a registration device for registering two-dimensional shape data, corresponding to three-dimensional shape data of a device, to a three-dimensional physical space, and said medical imaging device located in said three-dimensional physical space; and
   a fusion mechanism for fusing said two-dimensional shape data and said distorted two-dimensional radiographic images, to generate said two-dimensional simulated radiographic images.

2. The radiographic imaging system according to claim 1, further comprising:
   another medical imaging device for collecting said three-dimensional shape data.

3. The radiographic imaging system according to claim 2, wherein said another imaging device comprises an X-ray, computed tomography (CT) scanner.

4. The radiographic imaging system according to claim 1, wherein said two-dimensional shape data correspond to pre-operative radiographic data and said distorted two-dimensional radiographic images comprise intra-operative radiographic images.

5. The radiographic imaging system according to clam 4, wherein said pre-operative radiographic data comprises data of a surgical plan that includes a postion, an orientation, and said three-dimensional shape data of said device.

6. The radiographic imaging system according to claim 5, wherein said device comprises an implantable device for a patient.

7. The radiographic imaging system according to claim 1, wherein said two-dimensional shape data correspond to a two-dimensional radiographic image of a selected position and orientation of said devise.

8. The radiographic imaging system according to claim 1, wherein said two-dimensional simulated radiographic images comprise post-operative two-dimensional simulated radiographic images.

9. The radiographic imaging system according to claim 1, wherein said fusion mechanism generates said two-dimensional simulated radiographic images during surgery without correcting for distortion of said distorted two-dimensional radiographic images.

10. The radiographic imaging system according to claim 1, wherein said medical imaging device comprises at least one of a two-dimensional X-ray camera, a fluoroscope, and an X-ray flat panel detector.

11. The radiographic imaging system as in claim 1, wherein said fusion mechanism comprises a data processor.

12. A radiographic imaging system for fusing two-dimensional shape data, corresponding to pre-operative three-dimensional shape data of a device, with two-dimensional intra-operative radiographic images that are subject to distortion, comprising:

an intra-operative radiographic imaging device;

a registration device for registering said two-dimensional shape data to a three-dimensional physical space, and said intra-operative imaging device located in said three-dimensional physical space; and a fusion mechanism for fusing said two-dimensional shape data and said two-dimensional intra-operative radiographic images that are subject to distortion, to generate two-dimensional post-operative simulated radiographic images without correcting for distortion.

13. A radiographic imaging system for providing intra-operative visual evaluations of potential surgical outcomes, comprising:

a first medical imaging device for collecting pre-operative three-dimensional shape data of a device;

a second medical imaging device for collecting two-dimensional intra-operative radiographic images during surgery that are subject to distortion;

a registration mechanism for registering two-dimensional shape data, corresponding to said pre-operative three-dimensional shape data and a pre-operative surgical plan, to a three-dimensional physical space, and said second medical imaging device located in said three-dimensional physical space; and a fusion mechanism for fusing said two-dimensional shape data and said two-dimensional intra-operative radiographic images that are subject to distortion, without correcting for distortion, to generate two-dimensional simulated post-operative radiographic images during surgery.

14. A method of generating two-dimensional post-operative simulated radiographic images, comprising;

collecting two-dimensional shape data, corresponding to three-dimensional shape data of a device;

collecting two-dimensional intra-operative radiographic images that are subject to distortion;

registering said two-dimensional shape data to a three-dimensional physical space, and a medical imaging device located in said three-dimensional physical space; and fusing said two-dimensional shape data and said two-dimensional intra-operative radiographic images that are subject to distortion, to generate two-dimensional post-operative simulated radiographic images without correcting for distortion.

15. The method of generating two-dimensional post-operative simulated radiographic images according to claim 14, wherein said two-dimensional shape data corresponds to a surgical plan including a three-dimensional position, orientation, and shape of said device.

16. The method of generating two-dimensional post-operative simulated radiographic images according to claim 14, wherein said device is an implantable device for a patient.

17. A signal-bearing medium tangibly embodying a program of machine-readable instructions executed by a digital processing apparatus performing a method for computer-implemented generation of two-dimensional post-operative simulated radiographic images, comprising:

collecting pre-operative three-dimensional shape data of a device;

collecting two-dimensional intra-operative radiographic images that are subject to distortion;

registering two-dimensional shape data, corresponding to said pre-operative three-dimensional shape data of a device, to a three-dimensional physical space, and a medical imaging device located in said three-dimensional physical space; and fusing said two-dimensional shape data and said two-dimensional intra-operative radiographic images that are subject to distortion, to generate two-dimensional post-operative simulated radiographic images without correcting for distortion.

* * * * *